United States Patent [19]

Karl et al.

[11] Patent Number: 5,465,480

[45] Date of Patent: Nov. 14, 1995

[54] METHOD OF MANUFACTURING A GATING GRID

[75] Inventors: Manfred Karl; Ralf Burgartz, both of Leipzig, Germany

[73] Assignee: Bruker-Franzen Analytik GmbH, Bremen, Germany

[21] Appl. No.: 216,622

[22] Filed: Mar. 23, 1994

[30] Foreign Application Priority Data

Mar. 27, 1993 [DE] Germany .......................... 43 10 106.2

[51] Int. Cl.⁶ ..................................................... H01R 43/00
[52] U.S. Cl. ............................. 29/825; 29/602.1; 445/35; 445/36; 445/46
[58] Field of Search ................................... 29/825, 602.1; 445/35, 36, 46

[56] References Cited

U.S. PATENT DOCUMENTS

| | | |
|---|---|---|
| 3,788,721 | 1/1974 | Vause ......................................... 29/825 |
| 3,999,263 | 12/1976 | Marshall et al. . | |
| 4,633,083 | 12/1986 | Knorr et al. . | |
| 4,728,390 | 3/1988 | Yamamoto et al. ................... 29/602.1 |
| 5,280,175 | 1/1994 | Manfred . | |

FOREIGN PATENT DOCUMENTS

| | | |
|---|---|---|
| 4310106 | 10/1994 | Germany . |
| 58-108803 | 6/1983 | Japan ....................................... 29/825 |
| 2276490 | 9/1994 | United Kingdom . |

*Primary Examiner*—Carl J. Arbes
*Attorney, Agent, or Firm*—Bookstein & Kudirka

[57] ABSTRACT

A planar gating grid for an IMS spectrometer is constructed with two sets of comb-like grid elements. Each set is connected to an electrode and the sets are interdigitated to form the grid. Mechanical stability is provided by attaching the grid elements to an insulating support member. The gating grid is produced from a thin metal foil by cutting or etching the foil to produce a rigid grid structure where all of the elements are connected to both electrodes and the electrodes are separated by a stretcher member. After the rigid grid structure is affixed to the insulating support member, the grid elements are selectively severed from one of the two electrodes to form the interdigitated grid.

10 Claims, 4 Drawing Sheets

METHOD OF MANUFACTURING A GATING GRID

FIELD OF THE INVENTION

The invention concerns a gating grid for gating a stream of ions in which a dc voltage is applied between two sets of comb-like interdigitated grid wires arranged parallel to each other inside a grid plane, a method for manufacturing such a gating grid, and an ion mobility spectrometer (IMS) which incorporates such a gating grid.

BACKGROUND OF THE INVENTION

A gating grid, which is particularly used in IMS spectrometers, is, for example, known from U.S. Pat. No. 4,150,319. This known gating grid comprises two sets of parallel wires, each set consisting of a single, continuous wire which is strung back and forth across an insulating frame similar to the stringing of a tennis racquet. In this way, the wires of the two sets are fed through holes in the frame so that the parallel wire parts of the two sets alternate. When a voltage is applied between the two wires, electric fields with field lines between the alternately-biased wires are formed in the plane of the grid. These electric fields alternately change their direction, but are essentially directed perpendicular to the normal vector of the grid plane, which coincides with the direction of the ion current to be gated.

When compared to older types of gating grids, where the two wire sets were arranged in closely-spaced, but nevertheless different parallel planes (so-called Bradbury-Nielsen grids), this known grid has the advantage that almost no components of the electric field are present in the direction of the ion current (the axial direction of an IMS spectrometer). Therefore, the gating performance is considerably improved. In particular, when the grid is closed, the residual current, which in spectrometric use leads to a background signal, is noticeably reduced. The switching performance is also improved, i.e. when the grid is switched off, the current drops faster to zero.

However, this known gating grid has the disadvantage that it can only be produced in a costly way and with limited reproducibility. Moreover, for finite wire diameter, the gating plane is not precisely defined, leading to a broadening of the switching processes.

Therefore it, is an object of the invention to provide a gating grid of the kind mentioned above where the switching performance is improved.

It is another object of the invention to provide a method for the production of the improved grid in such a way that the gating grid can be produced in a simple, reproducible and reliable manner.

It is a further object to provide an improved IMS spectrometer which uses such a gating grid to achieve improved sensitivity, resolution and reliability.

SUMMARY OF THE INVENTION

The foregoing objects are achieved by a manufacturing method in which a grid structure is made from a thin planar metal foil by forming two sets of parallel elements or fingers. The fingers of each set are connected at one side to one of a pair of electrodes which are also formed from the foil and the fingers of each set are interdigitated. The parallel elements and the electrodes can be produced by cutting, etching, evaporation or electroplating.

Subsequently, the grid structure is glued (or a gas-tight contact is established by means of glass solder or glue) between the ends of two hollow insulating members, preferably fabricated of ceramic material. The insulating members each have a periphery at one end to which the grid structure is affixed. Illustratively, the insulating members have identical, preferrably circular, peripheries. The grid elements are affixed to the insulating members in such a way that the ends of the elements which are attached to the electrodes and the electrodes themselves protrude outside the insulting members.

In one embodiment, the grid elements are initially attached to both electrodes. Subsequently, the grid structure is affixed to the insulating members. Finally, the connections between the grid elements and the electrodes are selectively severed so that every other element remains connected to one electrode and these elements are interspersed with the remaining elements which are left connected to the other electrode. The resulting grid lies exactly inside a plane and the grid elements have only small production tolerances.

Preferably, the grid elements have only a narrow width in the area which lies inside the hollow insulating members, and are wider in the insulting member wall region. Alternate elements exhibit break point areas with predetermined or rated breaking strengths outside the wall region at the connection points of the elements and the electrodes. This construction has the advantage that, in the wall region, the elements can be placed across the periphery of the insulating members in a defined and safe way so that the connection of the two members safely fixes the grid, and that after fixation, the elements can be severed at the predetermined break points to form the comb-like interdigitated gating grid.

In another embodiment, the electrodes are initially both connected to, and stretched apart, by a stretcher section and separated only after the 15 gluing process is finished. This latter construction has the advantage that, during the first part of the production process, the grid is mechanically stabilized and therefore remains essentially planar.

Preferably, the insulating material of the hollow insulating members has a smaller thermal expansion coefficient than that of the planar metal grid and the gluing or the glass solder contact, respectively, is effected at an elevated temperature (compared to the subsequent operating temperature of the gating grid). This latter construction has the advantage that, due to the differing thermal expansion coefficients, the grid elements are pre-stressed, leading to an exact parallel alignment of the elements inside the grid plane.

Preferably, the connection of the two hollow insulating members, to which the grid is fixed, is effected in a gas-tight way so that the two insulating members directly form part of the walls of the reaction or drift chamber, respectively, and additional sealing means can be omitted.

In another preferred embodiment of the method, a foil mask with a multitude of identical grids is produced during a preliminary stage of the gating grid manufacturing process. This method of construction has the advantage that the grids are cost-effectively manufactured as mass products.

BRIEF DESCRIPTION OF THE DRAWINGS

FIG. 3 is a front view of a mask for series production of 50 grids using the grid blank according to FIG. 2a.

DESCRIPTION OF THE PREFERRED EMBODIMENT

Figure 1:
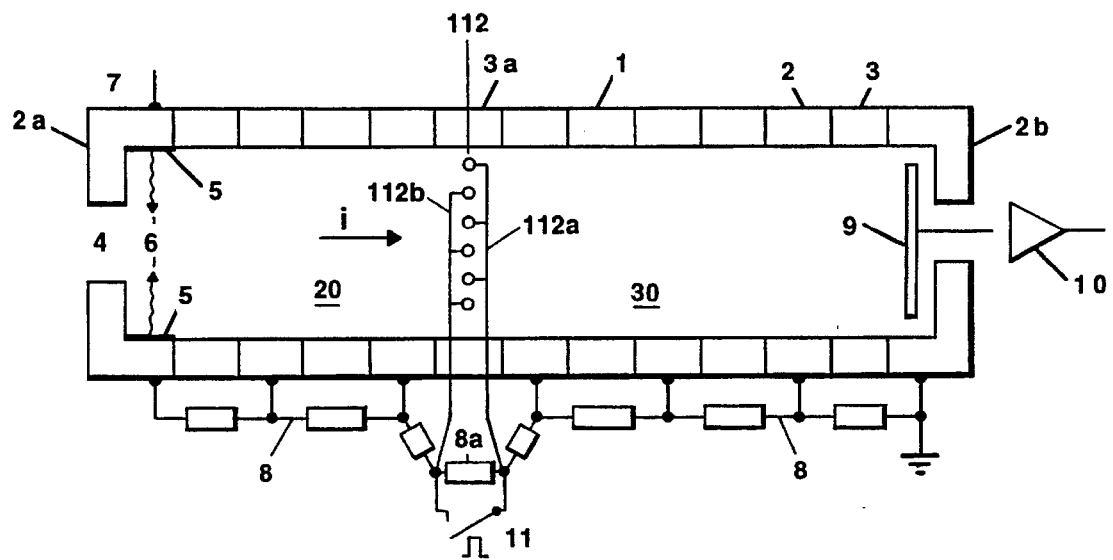
FIG.1 is a schematic representation of an IMS spectrometer tube with a gating grid.

In detail, FIG. 1 shows schematically an IMS spectrometer chamber 1 consisting of alternating metal 2 and ceramic 3 rings, known e.g. from U.S. Pat. No. 5,280,175. The first metal ring 2a represents the tube inlet with an inlet opening 4 for a measuring gas. On the inner surface of ring 2a there is attached a Ni-63 foil, whose beta-radiation 6 softly ionizes the molecules to be measured in the measuring gas. Onto the outside of ring 2a there is attached a high voltage connection 7 (typically 2 kV) for the ion transport in tube 1. The further metal rings 2 are electrically connected to the first ring 2a via a resistor cascade 8. This has the consequence that, in tube 1, an ion current 1 flows in an axial direction. The last ring 2b of the metal rings is grounded and carries an insulating ion collector 9 (typically a Faraday plate). The ion collector 9 is connected to a preamplifier 10 which transfers the amplified ion current i via an ADC (not shown) to a computer for processing.

One ring 3a of the ceramic rings 3 comprises a gating grid 112 according to the invention. The two halves 112a and 112b of the gating grid 112 (see FIG. 2c) are each electrically connected to one leg of a resistor 8a of resistor cascade 8. Resistor 8a can be shortened by a switch 11, so that the two grid halves 112a,b are at the same potential. When switch 11 is open, there is typically a potential difference of 100 V between the grid halves 112a,b and the grid 112 is closed to the ion current i.

Figure 2C:
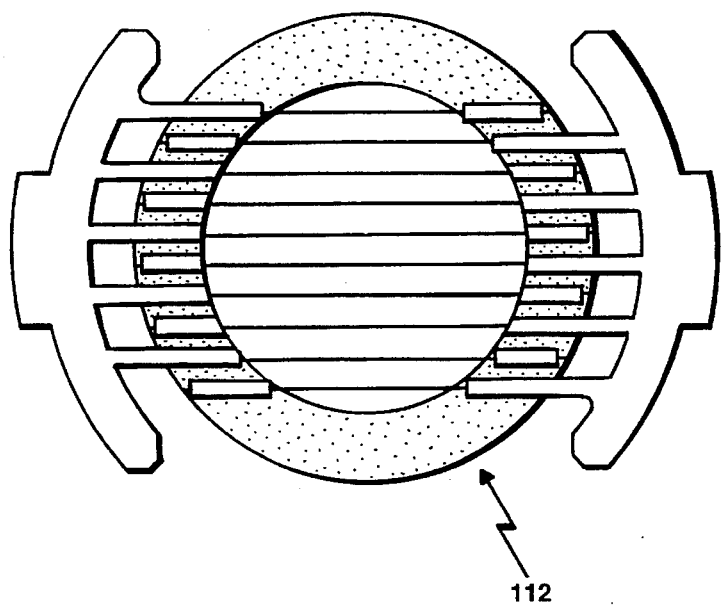
FIG. 2c) is a cross section between two tubes to which the grid is mounted which illustrates the steps of cutting through the gating grid after fixation and separation of the surplus components.
Figure 2A:
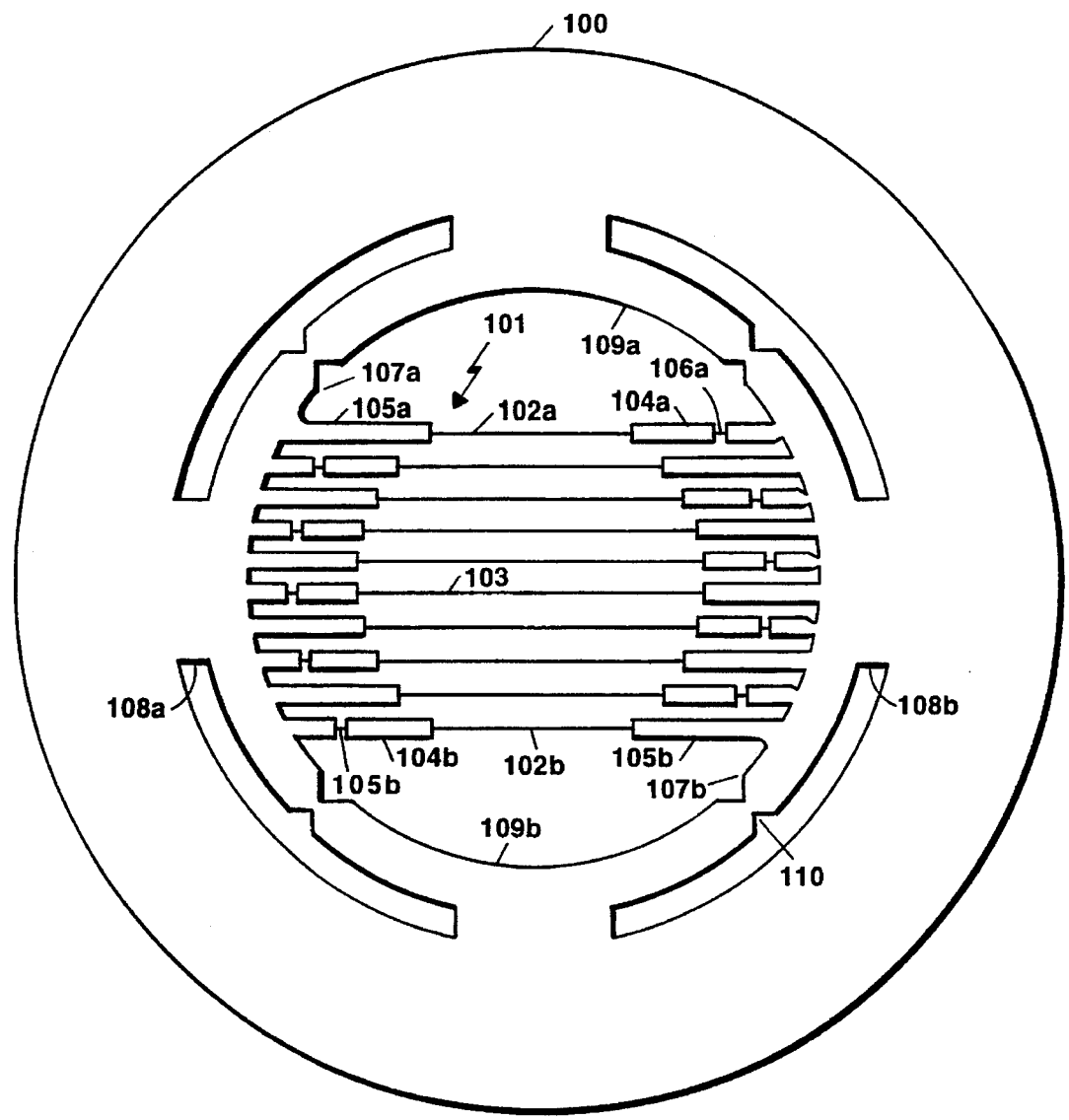
FIG. 2a) is a planar grid structure used in an intermediate stage of the method of the invention.

FIG. 2a shows a grid blank 100 formed of 50 micrometers thick steel foil with a planar grid pattern 101 which has been laser cut into the foil. Alternatively, nickel foil could also be used for the grid material, with both nickel and steel having the advantage of simple manufacturing and shaping to requested dimensions. In addition, a corresponding grid blank could also be manufactured according to one of the methods already mentioned above or equivalents thereof, e.g. galvanically, by evaporation, etching, or the like.

The blank 100 serves as a pre-stage for the gating grid 112 and comprises 10 elements, such as elements 102a, 102b, each of width 100 micrometers and spaced apart by a distance (lattice constant) of 1 mm in the central region 103 of the grid. The exact grid specifications can be varied, but preferably, the ratio between element spacing and element width of the grid is about 10 so that a transmission rate of about 90% during the on-state of the ion current is achieved. The element width of the elements of about 0.1 mm and element spacing about 1 mm are particularly preferred because they produce a grid which can be easily handled without risk of destruction.

Further, the number of grid elements can be varied but is preferably about 10. Such a grid can be used with conventional IMS spectrometers where the usual ion stream diameters are in the range of several millimeters to several centimeters in the grid plane and still achieve sufficiently narrow element distance and sufficient transmission.

Preferably, the thickness of the planar grid is between about 25 and 150 micrometers, in particular about 50 micrometers so that the grid may be easily handled yet the grid plane is very well-defined.

The elements 102a, 102b exhibit at their ends widened areas 104a, 104b, 105a, 105b, located outside the central region 103, which illustratively is circular region with a diameter of 11 mm. Every second widened area 104a, 104b has a notch 106a, 106b, whereas the other widened areas 105a, 105b are without notches. Consequently, each of the elements such as elements 102a, 102b has on one side a widened area with a notch, and on the other side an unnotched widened area so that on each side of the grid 101 the notched and unnotched widened areas alternate.

All elements 102a, 102b are connected on both sides, via the widened areas 104a, 104b, 105a, 105b to common arc-shaped electrodes 107a, 107b with tabs 108a, 108b for electrical connections. For mechanical stabilization of the grid 101, the electrodes 107a, 107b are connected via stretcher sections or arcs 109a, 109b, so that the electrodes 107a, 107b and the arcs 109a, 109b form a closed circle around the central region 103. At the transition points between the electrodes 107a, 107b and the arcs 109a, 109b there are again notches 110.

Figure 2B:
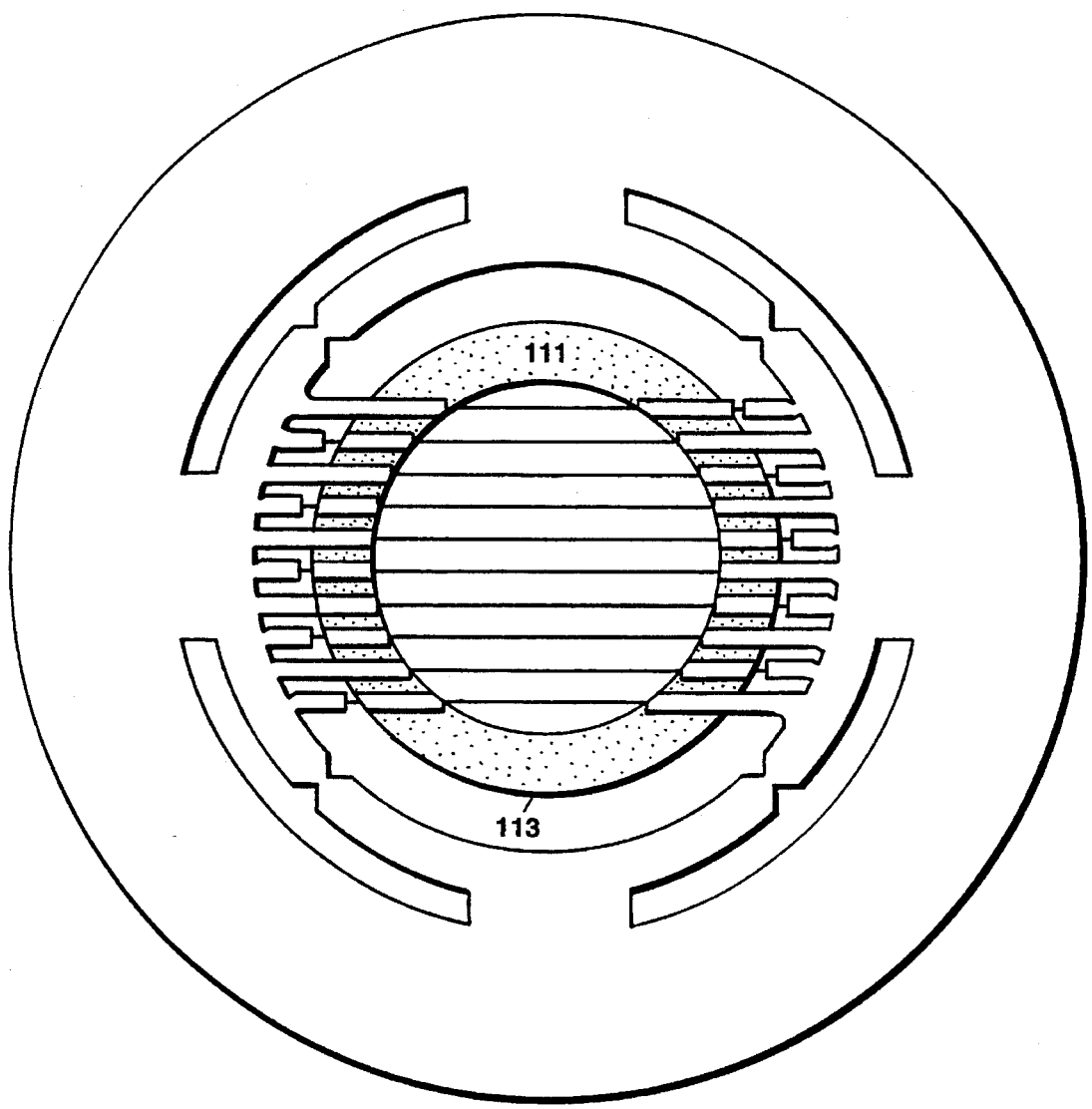
FIG. 2b) illustrates the step of positioning the grid onto an insulating hollow cylinder.

In FIG. 2b, the grid 101 of FIG. 2a is shown located relative to a ceramic tube 111 which tube has a circular cross-section and acts as a insulator support member. The grid is positioned adjacent to the end of the tube 111 such that, in FIG. 2b, an end view of the tube is shown behind the grid. The inner diameter of ceramic tube 111 coincides essentially with the central region 103 of the grid 101. The widened areas 104a, 104b, 105a, 105b of the 10 elements 102a, 102b are positioned on the wall 113 of the ceramic tube 111, whereby the positions of the notches 106a, 106b either approximately coincide with the outer diameter of ceramic tube 111, or lie somewhat outside the outer diameter. Arcs 109a, 109b, too, lie completely outside the outer diameter of ceramic tube 111. The insulating support members may have different cross-sectional shapes, but preferably hollow cylinders with a circular cross-section and an inner diameter of about 10 mm. The preferred shape has the advantage that the hollow cylinders can be part of the tube of an IMS spectrometer, which in general exhibits such a cross-sectional shape.

After grid 101 is located relative to the ceramic tube 111 according to FIG. 2b, a second ceramic tube of identical cross-section (not shown) is coaxially placed on top and connected to the first ceramic tube 111 at elevated temperature in a gas-tight manner, whereby in the region of the widened areas 104a, 104b, 105a, 105b the grid elements 1202a, 102b are fixed by this connection. In one illustrative example, this connection is effected by glass solder at a temperature of about 560° C., leading to a gas-tight ceramic-to-ceramic connection. However, alternative kinds of connections, e.g. gluing, can also be used. At the elevated temperature used to effect the connection, the steel of the planar grid 101 has expanded more than the ceramic of the tube 111. Accordingly, during the cooling down time period after the connection and fixation of the widened areas 104a, 104b, 105a, 105b to the ceramic tube 111 has been completed, the elements 102a, 102b in the central region are placed under tension, so that they remain absolutely planar and straight.

After cooling down and curing of the connection between the grid 101 and the tube 111 has been completed, the parts of the widened areas 105a, 105b between notches 106a, 106b and electrodes 107a, 107b are removed with the notches serving as predetermined or rated breakpoints. In the same way, the stretcher sections 109a, 109b are removed by severing the rated breakpoints 110 in order to produce the final gating grid as shown in FIG. 2c.

Although the arcs 109a and 109b are removed from the final assembly, the grid 101 is mechanically stabilized by the connection between the ceramic tubes 111 and the grid 101. For additional stabilization, the parts of the element widened areas 105a, 105b which protrude outside the ceramic tube 111 may now be glued to parts of electrodes 107a, 107b and to the outer wall of the ceramic tube 111 in order to prevent breaking off the widened areas or the electrodes, respectively.

As can be seen from FIG. 2c, a functioning gating grid 112 with comb-like interdigitated grid elements has been produced which is fixed between two coaxially connected ceramic tubes 111. This unit can now be used as part of an IMS spectrometer tube 1, whereby the gating grid 112 is introduced between the reaction chamber 20 and the drift chamber 30 of the IMS spectrometer tube 1 and whereby the ceramic tubes 111 each form part of the outer walls of these chambers 20, 30.

Figure 3:
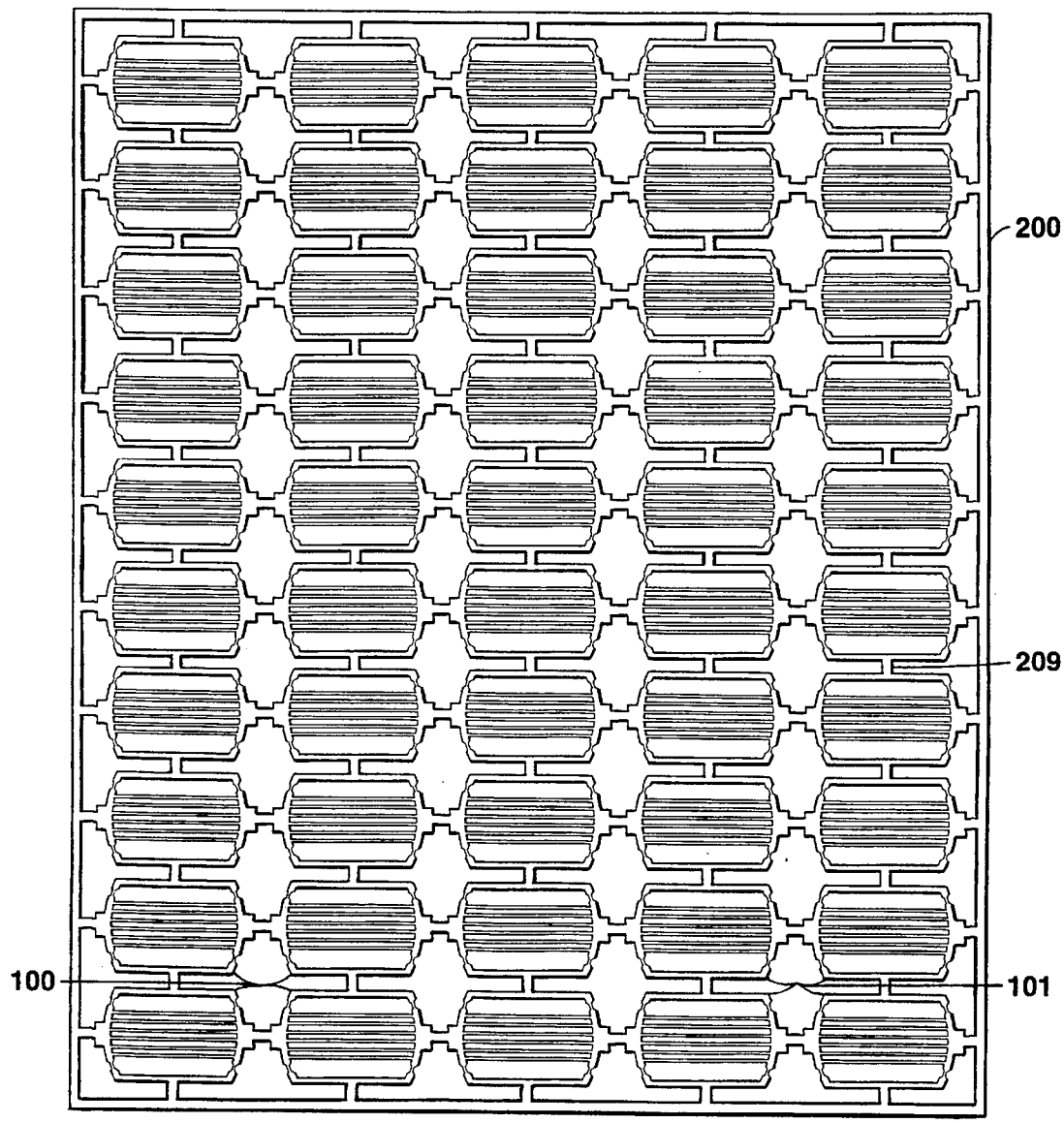

FIG. 3 shows how a multitude (illustratively 50) of grids 101 can be manufactured as a mass product from a metal foil mask as pre-stage of the gating grids 112. As shown, multiple grid blanks 100, like that shown in FIG. 2a, may be fabricated from a single sheet of material. From the cut, etched, evaporated or galvanically produced foil mask 200 the individual grids can be taken by severing the rated break points 209.

When a gating grid constructed in accordance with the principles of the invention is used in an IMS spectrometer, performance is improved due to better gating of the ion stream. Since the grid geometry of the inventive gating grid is better defined (in particular, the grid plane is defined more precisely) the result is a better resolution and a better signal-to-noise-ratio.

Preferably, the polarity of the voltage between the two electrodes can be reversed during the off-state in the IMS spectrometer. This has the advantage that accumulation of surface charges on the insulating components, in particular on the hollow cylinders, is largely avoided, which could lead to a field distortion.

Clearly, the features that have been described above can be used not only in the described combination but also in any other combination or individually without leaving the scope of the present invention. There is no intent that the invention should be limited to the features of the preferred embodiment described above.

What is claimed is:

1. A method for manufacturing a gating grid for ion mobility spectrometers, the gating grid having a first and a second electrode for connecting an electrical potential to the grid, the method comprising the steps of:

A. selecting a thin, planar metal foil;

B. removing portions of the foil to form a grid pattern in the foil, the grid pattern having a first comb-like grid element set with a first plurality of grid elements arranged in parallel and spaced apart and connected to the first electrode, the first plurality of grid elements interdigitated with a second comb-like grid element set with a second plurality of grid elements arranged in parallel and spaced apart and connected to the second electrode;

C. selecting a first hollow insulating support member having a periphery with a cross-sectional area which encloses the first and the second grid element sets but excludes the first and second electrodes; and D. affixing the foil to the periphery.

2. A method according to claim 1 wherein step B comprises the steps of:

B1. removing the portions from the foil by cutting the portions from the foil.

3. A method according to claim 1 wherein step B comprises the steps of:

B2. removing the portions from the foil by etching the portions from the foil.

4. A method according to claim 1 wherein step B comprises the steps of:

B3. forming the first electrode and the second electrode in the foil.

5. A method according to claim 4 wherein step B comprises the steps of:

B4. forming the grid pattern with a stretcher section of the foil connected to and separating the first electrode and the second electrode.

6. A method according to claim 5 wherein the method further comprises the step of:

F. removing the stretcher section.

7. A method according to claim 1 wherein step B comprises the steps of:

B5. forming the grid pattern so that the first plurality of grid elements is connected to both the first electrode and the second electrode and the second plurality of grid elements is connected to both the first electrode and the second electrode.

8. A method according to claim 7 wherein the method further comprises the steps of:

F. severing the connection of the first plurality of grid elements to the second electrode; and G. severing the connection of the second plurality of grid elements to the first electrode.

9. A method according to claim 1 further comprising the step of:

H. affixing a second hollow insulating support member having a periphery to the periphery of the first insulating support member to the foil so that the foil is sandwiched between the first and the second hollow insulating support members.

10. A method according to claim 1 wherein step B comprises the steps of:

B6. removing portions of the foil to form a plurality of grid patterns in the foil, each of the plurality of grid patterns comprising
    a first electrode,
    a second electrode,
    a first comb-like grid element set with a first plurality of grid elements arranged in parallel and spaced apart and connected to the first electrode,
    a second comb-like grid element set with a second plurality of grid elements arranged in parallel spaced apart and interdigitated with the first plurality of grid elements and connected to the second electrode.

* * * * *